US012752102B1

(12) United States Patent
Covalin et al.

(10) Patent No.: US 12,752,102 B1
(45) Date of Patent: Oct. 6, 2026

(54) DISPOSABLE ELECTRODES FOR PORTABLE STIMULATION DEVICES AND SYSTEMS AND METHODS FOR REPLACEMENT OF THE DISPOSABLE ELECTRODES

(71) Applicant: Spark Biomedical, Inc., Dallas, TX (US)

(72) Inventors: Alejandro Covalin, Los Angeles, CA (US); Meghan R. Luellen, Charlotte, NC (US); Jared Wettenstein, Houston, TX (US)

(73) Assignee: Spark Biomedical, Inc., Dallas, TX (US)

( * ) Notice: Subject to any disclaimer, the term of this patent is extended or adjusted under 35 U.S.C. 154(b) by 0 days.

(21) Appl. No.: 19/240,739

(22) Filed: Jun. 17, 2025

(51) Int. Cl.
*A61N 1/04* (2006.01)
*A61N 1/36* (2006.01)

(52) U.S. Cl.
CPC ....... *A61N 1/0496* (2013.01); *A61N 1/36025* (2013.01)

(58) Field of Classification Search
CPC ... A61N 1/0496; A61N 1/0456; A61N 1/0472
See application file for complete search history.

(56) References Cited

U.S. PATENT DOCUMENTS

| | | | |
|---|---|---|---|
| 3,746,004 A | 7/1973 | Jankelson | |
| 4,300,575 A | 11/1981 | Wilson | |
| 4,580,339 A | 4/1986 | Ioffe | |
| 4,979,517 A | 12/1990 | Grossman et al. | |
| 5,203,330 A | 4/1993 | Schaefer et al. | |
| 8,903,494 B2 | 12/2014 | Goldwasser et al. | |
| 9,131,895 B2 | 9/2015 | Grob et al. | |
| 10,426,945 B2 | 10/2019 | Tyler et al. | |
| 2017/0049397 A1* | 2/2017 | Sun | G01K 7/427 |

(Continued)

FOREIGN PATENT DOCUMENTS

WO WO2021011165 A1 1/2021

OTHER PUBLICATIONS

Bravo-Iniguez, Carlos E., et al., "Vagus nerve stimulation primes platelets and reduces bleeding in hemophilia A male mice", Nature Communications, 2023, 14:3122, 12 pages.

(Continued)

*Primary Examiner* — Brian T Gedeon
(74) *Attorney, Agent, or Firm* — Secant IP, P.L.L.C.

(57) ABSTRACT

In an illustrative embodiment, a disposable electrode unit for releasably adhering to a wearable stimulation device includes a structural support layer having an shape configured to align with a tissue region of a wearer, the structural support layer including openings for aligning with electrode contacts of the stimulation device, and adhesive layer(s) each composed of one or more materials configured to provide electrical conductivity and/or adhesion. The adhesive layer(s) may be disposed to fill the openings, thereby enabling electrical conduction from the electrode contacts to tissue regions of the wearer. A device-facing surface of the adhesive layer(s) may be configured to releasably adhere to surface(s) of the stimulation device including the electrode contacts, and a skin-facing surface of the adhesive layer(s) may be configured to releasably adhere to the tissue regions of the wearer.

14 Claims, 8 Drawing Sheets

(56) References Cited

U.S. PATENT DOCUMENTS

| | | | | |
|---|---|---|---|---|
| 2017/0368329 | A1 | 12/2017 | Tyler et al. | |
| 2020/0237309 | A1* | 7/2020 | Golda .................. | A61B 5/0002 |
| 2020/0238085 | A1* | 7/2020 | Khodaparast ........ | A61N 1/0492 |
| 2022/0212012 | A1 | 7/2022 | Manogue | |
| 2023/0026037 | A1 | 1/2023 | Iñaki et al. | |
| 2024/0285944 | A1 | 8/2024 | Covalin et al. | |

OTHER PUBLICATIONS

Wang, Chenxi, et al., “Brain Stimulation”, Elsevier, May-Jun. 2023, vol. 16, Issue 3, pp. 695-697.

International Search Report and Written Opinion received in International Application No. PCT/US2025/033989, mailed Nov. 18, 2025, 19 pages.

* cited by examiner

DISPOSABLE ELECTRODES FOR PORTABLE STIMULATION DEVICES AND SYSTEMS AND METHODS FOR REPLACEMENT OF THE DISPOSABLE ELECTRODES

BACKGROUND

Disposable electrodes used for both electrical stimulation and biological signal recording across the skin rely predominantly on some sort of a single point connection, in most cases a cable connector such as metallic snap or rod connectors, to interface with their respective devices. While recording electrodes, such as those used in electrocardiogra (ECG) or electroencephalography (EEG), may benefit from concentrated signal input through these single-point connections, this is not the case for electrodes used for stimulation. In general, both stimulation and recording electrodes share common limitations inherent to this traditional connector design.

These connection points frequently experience oxidation and corrosion, requiring regular cleaning and maintenance of the device contacts. While the hydrogel (the most common used material for skin contact) layer in traditional electrodes is isolated to the skin-facing side, the metal-to-metal contact points between the electrode snap or rod and the device connector are still susceptible to environmental factors that can degrade connection quality over time.

A significant limitation of current electrode designs stems from their point-contact interfaces, which necessitate additional current-spreading layers such as printed silver/silver chloride, carbon, and/or metallic meshes or films. These layers add considerable manufacturing complexity and cost. The need for such current-spreading layers arises from the substantial difference in conductivity between the skin-contacting layer (typically hydrogel) and the skin/electrode interface. Without these additional layers, stimulation electrodes would create “hot spots” typically close to the connection point-areas where current density is significantly higher than in surrounding regions. This uneven current distribution could compromise both the efficacy and safety of therapeutic applications.

Furthermore, the incorporation of connectors (such as snaps, rod plugs, or cable assemblies) requires additional pre- and/or post-processing steps in the manufacturing process. These steps necessitate specialized machinery, increase production time, and add complexity to the manufacturing line. Such requirements not only increase direct production costs but also demand additional quality control measures and raise the potential for manufacturing defects.

While recording electrodes may benefit from concentrated signal acquisition at a single point, they still incorporate these additional conductive layers and connection components, adding unnecessary cost and complexity to their manufacturing process. The inclusion of current-spreading layers and connectors impacts not only material costs through the use of expensive conductive materials but also requires specialized printing or deposition processes, demanding quality control measures for layer uniformity, and increasing both inventory management complexity and the likelihood of manufacturing defects.

SUMMARY OF ILLUSTRATIVE EMBODIMENTS

In one aspect, the present disclosure relates to the manufacture and design of disposable electrodes. The electrode may include two or three layers working in concert. The disposable electrode may be configured to releasably attach to a contact point on a stimulation device, such as a wearable neurostimulation device.

In some embodiments, a disposable electrode includes a conductive adhesive layer configured to provide both electrical conductivity and mechanical attachment to contacts of a corresponding stimulation device. The contacts, for example, may include contact surfaces or contact features of the stimulation device. The conductive adhesive layer may allow the disposable electrode to be easily removable without leaving residue. For example, the conductive adhesive layer may involve a dry, double-sided adhesive.

In some embodiments, a disposable electrode includes a flexible structural layer configured to serve as a support while maintaining flexibility for conforming to complex anatomical surfaces. The flexible structural layer may be a flexible perforated structural substrate.

In some embodiments, a disposable electrode includes a conductive layer designed for skin contact and current delivery to or signal reception from the tissue. The conductive layer, in some examples, may be a hydrogel or dry adhesive layer. The conductive layer may be the same conductive layer as the conductive layer designed for device contact or a different layer.

The above-described layered construction eliminates the need for traditional connectors and current-spreading layers, enabling the electrode to be manufactured using standard converting equipment, similar to adhesive bandage production lines. The ability to manufacture the disposable electrodes using commonly available techniques and a single production line significantly reduces manufacturing complexity and cost.

In one aspect, the present disclosure relates to an alignment case configured for electrode application to a stimulation device. The alignment case, for example, may include loading mechanisms that simplify electrode placement while ensuring proper alignment with contacts of the stimulation device. In addition to precision-aligned loading of new disposable electrodes onto the stimulation device, in some embodiments, the alignment case includes charging circuitry for device charging. The alignment case, for example, may incorporate charging safety features that eliminate the need for expensive isolation circuits in the stimulation device itself.

In some embodiments, the alignment case includes one or more retention features for releasably receiving the stimulation device. The alignment case, for example, may include at least one depression or well conforming to a shape of a portion of the stimulation device. In another example, the alignment case may include at least one raised retention feature configured to releasably receive corresponding features of the stimulation device.

The alignment case, in some embodiments, includes one or more retention features for releasably receiving a disposable electrode. The alignment case, for example, may include one or more depressions or wells and/or one or more raised retention features for releasably receiving the disposable electrode. In illustration, the retention features may include adhesive, interfering, and/or frictional features overcome upon adhering the disposable electrode to one or more contact surfaces of the stimulation device. For example, the disposable electrode may be loaded into a lid portion of the alignment case, and the stimulation device may be loaded into a receptable portion of the alignment case. Upon closing the lid, exposed adhesive of the disposable electrode may align with and adhere to electrode contacts of the stimulation device. The electrode contacts may include contact features (e.g., raised bumps, posts, etc.) and/or contact surfaces (e.g., metal regions substantially aligned with or flush with a surface of the surrounding surface area of the stimulation device).

Together, the above-described aspects create a more accessible and user-friendly therapeutic electrical stimulation system. These innovations address both technical limitations of current electrode designs and practical barriers to widespread adoption of therapeutic neurostimulation devices. Various embodiments described herein involve systems and methods that are not only more cost-effective to manufacture but also more reliable and easier to use. The resulting reduction in both production costs and user complexity enables broader market adoption and improved accessibility to therapeutic neurostimulation. Such accessibility is particularly important for applications requiring regular or frequent use, where cost and ease of use are critical factors in treatment compliance and business sustainability, ultimately benefiting both users and the company commercializing aspects of the present disclosure.

The foregoing general description of the illustrative embodiments and the following detailed description thereof provide mere examples of various aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. In the drawings.

DETAILED DESCRIPTION OF ILLUSTRATIVE EMBODIMENTS

Figure 1:
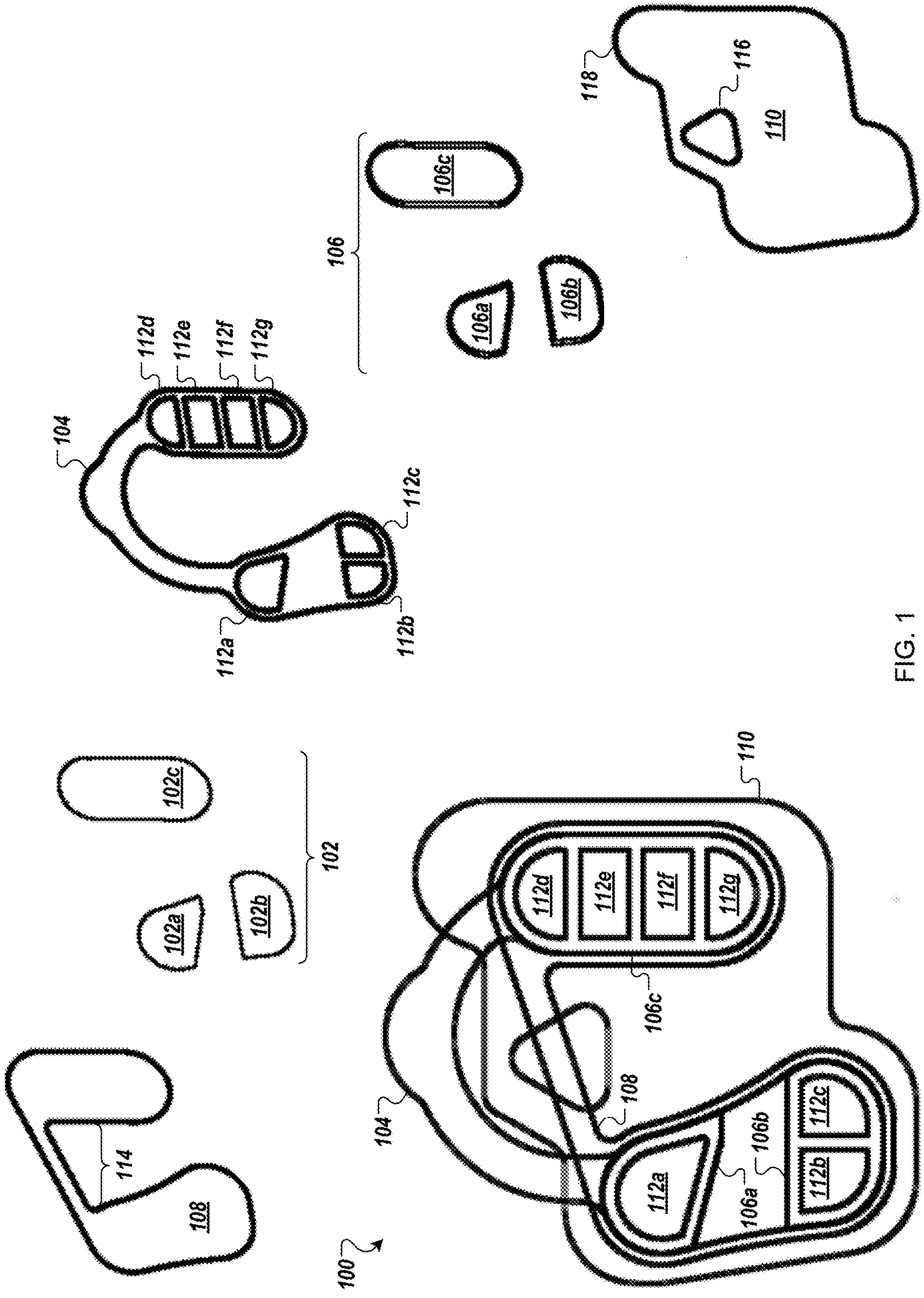
FIG. 1 is a diagram of an example disposable three-electrode unit in both an assembled view and an exploded view.

The description set forth below in connection with the coordinating drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

As used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Further, the terms "approximately," "about," "proximate," "minor variation," and similar terms generally refer to ranges that include the identified value within some margin, such as, in some examples, 20%, 10%, or 5% in certain embodiments, as well as any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

In some embodiments, a disposable electrode features a novel two- or three-layer design that eliminates the need for traditional connectors and current-spreading layers. The disposable electrode may be designed for releasable attachment to a stimulation device such that the disposable electrode is in conductive contact with at least one electrode contact of the stimulation device. The disposable electrode may be designed for one or more uses. A multi-use scenario, for example, may involve delivering two or more stimulation sessions to a patient throughout a day, where each day a new disposable electrode is attached to the stimulation device.

In the layered disposable electrode design, each layer serves one or more specific functions while contributing to the overall manufacturing simplicity. In illustration, the disposable electrode may include a device-interfacing adhesive conductive layer configured to interface with an electrode contact on a stimulation device, a structural support layer configured to maintain a desired level of rigidity and/or flexibility to suit the electrode's design and intended attachment point on the skin of a patient, and a skin-interfacing adhesive conductive layer configured to interface with the patient's skin. The device-interfacing adhesive conductive layer may be the same material layer as the skin-interfacing adhesive conductive layer in some embodiments. Additional layers may be included, such as adhesive backing layers (e.g., paper liner) protecting the adhesive material on each of the device-interfacing adhesive conductive layer and the skin-interfacing adhesive conductive layer.

FIG. 1 illustrates an example disposable three-electrode unit 100 in both an assembled view and an exploded view. The layers of the disposable electrode assembly 100, as described in further detail below, may be engineered to work in concert, providing optimized electrical, mechanical, and interface characteristics. In the illustrated example, these layers form an asymmetric shape designed to wrap partially around a user's ear, with specific regions for stimulating predetermined anatomical targets. The three-electrode unit 100 includes a device-facing adhesive conductive layer 102 including three contact-interfacing surfaces 102*a*-102*c*, a structural layer 104, and a skin-facing adhesive conductive layer 106 including three skin-interfacing surfaces 106*a-c*. As illustrated, a first contact-interfacing surface 102*a* of the device-facing adhesive conductive layer 102 is sized and shaped generally the same as a first skin-interfacing surface 106*a* of the skin-facing adhesive conductive layer 106 and configured to be layered in contact with each other via an opening 112*a* in the structural layer 104, as shown for example in the assembled view of the three-electrode unit 100. Similarly, a second contact-interfacing surface 102*b* is shaped generally the same as a second skin-interfacing surface 106*b* and configured to be layered in contact with each other via a set of openings 112*b*, 112*c* in the structural layer 104. Finally, a third contact-interfacing surface 102*c* is shaped generally the same as a third skin-interfacing surface 106*c* and configured to be layered in contact with each other via a set of openings 112*d*-112*g* in the structural layer 104.

The device-facing adhesive conductive layer 102, in some implementations, includes a dry, double-sided conductive adhesive, providing direct electrical connection to corresponding metallic contacts of a stimulation device. This device-facing adhesive conductive layer 102 may include materials designed to maintain a sufficiently strong adhesion to ensure reliable electrical contact while featuring controlled adhesion characteristics that allow for easy removal despite its holding force. In illustration, the strength of adhesion may be between 50 and 250 N/m 180-deg peel force vs. steel. The device-facing adhesive conductive layer 102 may be configured peel off of the stimulation device cleanly after use, without leaving residue. Further, the device-facing adhesive conductive layer 102 may be configured to prevent oxidation of the metallic contacts of the stimulation device through a non-corrosive composition. In an illustrative example, the device-facing adhesive conductive layer 102 may be formed of or include Flexcon® Omni-Wave™ dry biomedical electrode material by Flexcon Company, Inc. of Spencer, MA.

In some implementations, the structural layer 104 provides a flexible perforated structural substrate, lending mechanical support and stability while maintaining a level of flexibility appropriate for anatomical conformity (in the illustrated circumstance, for over the ear adhesion). The structural layer 104 may be formed of or include biocompatible plastics such as, in some examples, polyethylene terephthalate (PET), nylon, polytheylene (PE), polyurethanes, polydimethylsiloxane, and/or polytetrafluoroethylene. The structural layer 104, for example, may have a thickness between 0.02 and 0.15 millimeters. In an illustrative example, the structural layer 104 may be formed of 0.05 millimeter PET.

Each conductive, adhesive surface (e.g., the surfaces of layers 102, 106) may align with one or more strategically-aligned perforations of the structural layer 104, enabling electrical continuity/conductivity between the adhesive surface(s) of the skin-facing conductive, adhesive layer 106 and the device-facing conductive, adhesive layer 102 while serving as an integration platform for the overall construction. As illustrated in the assembled view of the example disposable electrode assembly 100, for example, the first skin-interfacing surface 106*a* covers and extends slightly beyond the opening 112*a*, the second skin-interfacing surface 106*b* covers and extends slightly beyond the openings 112*b*, 122*c*, and the third skin-interfacing surface 106*c* covers and extends slightly beyond the openings 112*d-g*.

In some implementations, the skin-facing conductive, adhesive layer 106 includes one or more conductive and/or adhesive materials configured to ensure reliable and consistent skin contact while providing appropriate impedance for current delivery and maintaining user comfort. The skin-facing conductive, adhesive layer 106, further, may include materials configured to allow for repositioning without discomfort to the patient or notable degradation in adhesion properties upon final positioning. The ability to relocate the disposable electrode assembly 100 on the patient is particularly important for applications requiring precise positioning, as it allows users to adjust the electrode placement during the initial application period, allowing for ensuring therapeutic contact while maintaining electrode functionality. For example, the adhesive material(s) of the skin-facing conductive-adhesive layer 106 may provide staged adhesion for precise positioning, where full adhesive properties active with contact to the atmosphere and/or the skin. In illustration, the adhesive material(s) may allow for position adjustment while the material(s) is increasing in temperature toward body temperature. After reaching full adhesion, the hydrogel may maintain secure adhesion to the skin while remaining comfortable during extended wear periods (e.g., over an hour, between one and four hours, up to eight hours, up to twelve hours, or up to at least twenty-four hours).

In some embodiments, the skin-facing conductive adhesive layer 106 is a dry adhesive layer, for example using the Flexcon® Omni-Wave™ dry biomedical electrode material. The skin-facing conductive adhesive layer 106, in some embodiments, is a hydrogel layer, such as the Axelgaard AG2500 series of multi-use high-tack hydrogels available from Axelgaard Manufacturing Co., Ltd. of Fallbrook, CA. The hydrogel layer may be composed, for example, of a multilayered hydrogel assembly, providing both electrical conductivity and double-sided adhesion, where one side is configured to adhere to skin and the other side is configured to adhere to a base substrate (e.g., the stimulation device).

Although referenced herein as "layer" in a singular sense, in general, both the device-facing conductive adhesive layer 102 and the skin-facing conductive adhesive layer 106 are not necessarily provided in a monolayer form; rather, they may be composed of multiple material layers. For example, an electrode unit-contacting surface of either of the layers 102 or 106 may be formed of a different material than an opposite surface either of the layers 102 or 106. Further, a carrier material may be disposed between the electrode unit-contacting surface and an externally-facing (e.g., protective material covered) surface of either layer 102 or 106.

In some embodiments, a disposable electrode is manufactured with only two functional (e.g., non-protective) layers. In this circumstance, a single layer or material may function as both the skin-facing conductive adhesive layer 106 and the device-facing conductive adhesive layer 102, using one or more types of material suitable for both skin contact and metal contact. The material, further, may be suitable for removal from the metal contact for disposing. The two-layer disposable electrode embodiment, further, may include a combination conductive adhesive layer replacing layers 102 and 106 that is designed to adhere to the base layer 104 on a skin-facing side of the base layer 104 and adhere to the device through the openings 112 of the base layer 104. The combination conductive adhesive layer, for example, may fill the openings 112 of the base layer 104. Further to this illustrative example, the openings 112 may include smaller perforations or mesh, such as a honeycomb or grid pattern of openings, thereby providing a larger surface for the adhesive conductive layer to adhere to on the base layer 104 while exposing adequate empty area to have electrical continuity and adhesion to the device metal electrodes via the openings. Continuing with the illustrative example, in addition to the openings 112, one or more further perforations and/or openings may be provided through the base layer 104 to increase adhesion between the disposable electrode unit 100 and the stimulation device. The further perforations and/or openings may include a perforated design or mesh pattern as discussed in relation to the openings 112. The perforated design of the openings 112 and/or the further perforations and/or openings, for example, may provide sufficient adhesion to the base layer 104 as well as sufficient adhesion, via the perforations and/or further openings, to the device, including the device electrical contacts (e.g., contacts 216 and 218 of FIG. 2B), such that when the user removes the device from their skin, at least a majority of the adhesive conductive layer remains adhered to the base layer 104 and not on the skin. In some two-layer disposable electrode unit embodiments, the surface of the base layer 104 in contact with the adhesive conductive layer (e.g., the skin-facing surface of the base layer 104) may be treated to enhance the adhesion between the base layer 104 and the conductive adhesive layer. The treatment, for example, may include additional adhesive material or a surface treatment (e.g., ridges, roughness, bumps, etc.) designed to increase surface area of the skin-facing surface of the base layer 104.

In some implementations, to protect the device-facing adhesive conductive layer 102 prior to use (or, in a two-layer embodiment, the other side of the skin-facing adhesive conductive layer 106 exposed through the openings 112), a rear backing layer 108 is positioned over the exterior surface of the device-facing adhesive conductive layer 102. The rear backing layer 108 may include one or more features to assist in manual removal of the rear backing layer 108 prior to applying the disposable electrode assembly 100 to the stimulation device. For example, the rear backing layer 108 includes a connecting portion 114 that may be grasped by a user to remove the rear backing layer 108 from the disposable electrode assembly 100.

Similarly, to protect the skin-facing adhesive conductive layer 106, in some implementations, a front backing layer 110 is positioned over the exterior surface of the skin-facing adhesive conductive layer 106. The front backing layer 110 may include one or more features to assist in manual removal of the front backing layer 110 prior to use of the stimulation device. For example, the front backing layer 110 includes an opening 116 that may assist a user in pulling the front backing layer 110 away from the disposable electrode assembly 100.

Although described as a particular implementation in relation to the disposable electrode assembly 100, Table 1, below, illustrates example materials and corresponding functionality for manufacturing a three-layer, disposable electrode. The disposable electrode may be implemented as a unit, as described above, including any number of individual electrodes and designed to contact various surfaces on the body of a human or animal.

TABLE 1

Example Layers of a Disposable Electrode

| Layer | Material | Functionality |
|---|---|---|
| Device Interface Layer | Dry Double-Sided Conductive Adhesive | Provides direct electrical connection to metallic contacts of stimulation device;<br>Maintains strong adhesion for reliable electrical contact;<br>Features controlled adhesion allowing easy removal;<br>Peels off cleanly without residue;<br>Prevents oxidation through non-corrosive composition. |
| Structural Layer | Flexible Perforated Substrate | Provides mechanical support and stability;<br>Maintains flexibility for anatomical conformity;<br>Features perforations for inter-layer conductivity;<br>Serves as integration platform for other layers. |
| Skin Interface Layer or Multi-Purpose Skin & Device Interface Layer | Hydrogel | Ensures consistent, reliable skin contact;<br>Provides appropriate impedance for current delivery;<br>Maintains comfort during wear;<br>Permits initial repositioning while maintaining functionality. |

As described, the disposable electrode assembly 100 may be designed for removable attachment to a stimulation device configured for wearing around a patient's ear. FIG. 2A through 2F illustrate a stimulation device 200 and system for installing disposable electrodes onto the stimulation device.

Figure 2A:
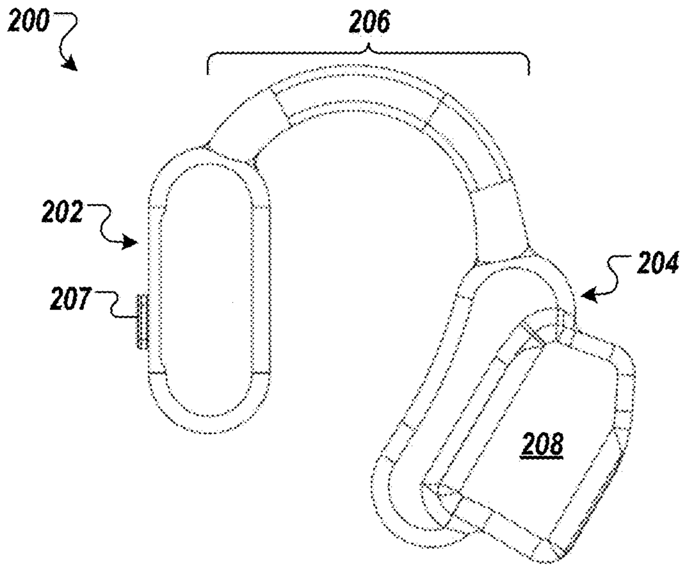
FIG. 2A is a diagram of an example stimulation device.

Turning to FIG. 2A, the stimulation device 200 may be positioned over a user's ear to deliver electrical auricular neurostimulation. The stimulation device 200 includes a forward stimulation pad 202 (disposed on an opposite surface to the visible surface in the view FIG. 2A) designed to be worn against the skin in front of the ear, a rear stimulation pad 204 (disposed on an opposite surface to the visible surface in the view FIG. 2A) designed to be worn against the skin behind the ear, and an over-the-ear connector 206 to provide electrical communication between the rear stimulation pad 204 and the forward stimulation pad 202. A power and/or controller unit 208 may provide electrical charge (e.g., a battery) and/or stimulation control to the electrodes of the stimulation device 200. The power unit 208, in some embodiments, powers distributed control circuitry provided upon additional surfaces of the stimulation device 200. In further embodiments, a portion of the control circuitry may be provided in a separate wired or wireless unit. For example, the power and/or controller unit 208 may include wireless communications circuitry for receiving control instructions from a separate control device (e.g., smart phone application, dedicated controller, etc.). A manual control 207 (e.g., push button) may be provided to power the stimulation device on/off and/or adjust stimulation parameters.

Figure 2B:
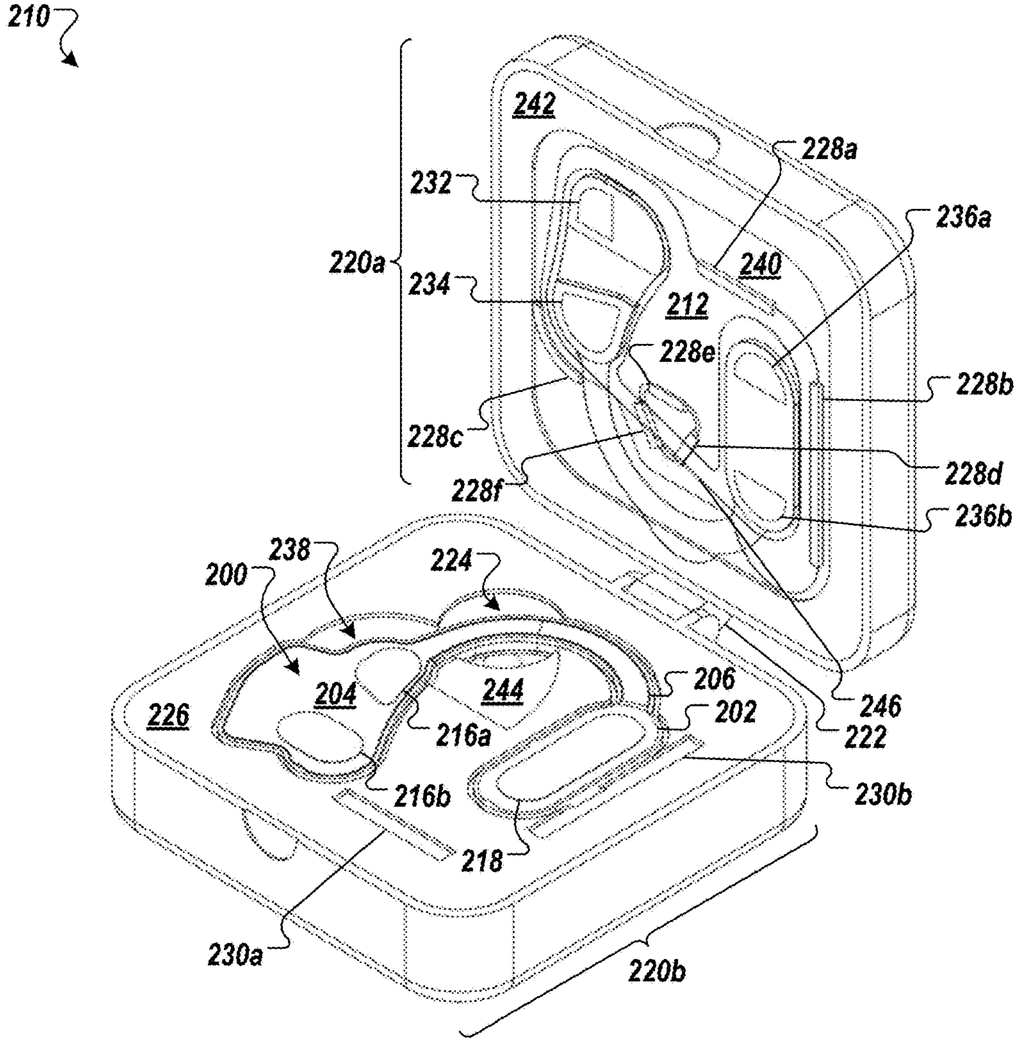
FIG. 2B through FIG. 2F illustrate various views of an example case for installing disposable electrodes onto a stimulation device.

FIG. 2B illustrates an open, offset view of a case 210 with the stimulation device 200 set within. As illustrated a reverse side (e.g., skin-facing side) of the stimulation device 200 is visible. The skin-facing surface of the stimulation device 200 includes a set of electrical contacts, with two electrical contacts 216*a*, 216*b* disposed on the rear stimulation pad 204 and one electrical contact 218 disposed on the forward stimulation pad 202. The case 210 is also holding a disposable electrode assembly 212 (e.g., similar to the disposable electrode assembly 100 of FIG. 1). The case 210, for example, may be used to align and fix the electrodes of the disposable electrode assembly 212 to the set of electrical contacts 216, 218.

As illustrated, the case 210 includes a first (e.g., upper, as illustrated) half 220*a* (e.g., portion, not necessarily denoting 50% of the case but representing one of two connected three-dimensional units which fit together to create an enclosure) holding the disposable electrode assembly 212 and a second (e.g., lower) half 220*b* holding the stimulation device 200. The first and second halves 220*a*, 220*b* are hingedly connected at a hinge joint 222.

The second half 220*b* of the case 210, in some implementations, includes a depression for receiving the stimulation device 200. A deep rounded opening 224 in an interior surface 226 of the second half 220*b* of the case 210 may provide access for grasping the connector 206 of the stimulation device 200 to remove the stimulation device 200 from the case 210.

The first half 220*a* of the case 210, in some implementations, includes a set of retention members 228*a-f* (e.g., tabs, lips, clips, hooks, etc.) for releasably securing the disposable electrode assembly 212 into the first half of the case 210. The retention members 228*a-f*, as illustrated, include a raised edge configured to releasably receive a corresponding edge portion of the disposable electrode assembly 212. In other embodiments, the retention members 228*a-f* may include flexible and/or spring-loaded (e.g., hinged) members that raise up to accept edge features of the disposable electrode assembly 212 and retain the disposable electrode assembly 212 via spring force or frictional force. The retention members 228*a-f*, in another example, may include a tacky and/or texturized surface facing the disposable electrode assembly 212 to apply frictional or low level adhesive force in retaining the disposable electrode assembly 212 in place. The first two retention members 228*a*, 228*b*, as illustrated, align with corresponding depressions 230*a*, 230*b* extending below the interior surface 226 of the second half 220*b* of the case 210. The retention members 228*a-f*, for example, may be designed to exert a retaining force on the disposable electrode assembly 212 that is at least ten percent greater than a maximum force generated by the electrode assembly's mass during closure of the case 210 at angular velocities up to approximately eight to 10 radians per second.

Figure 2C:
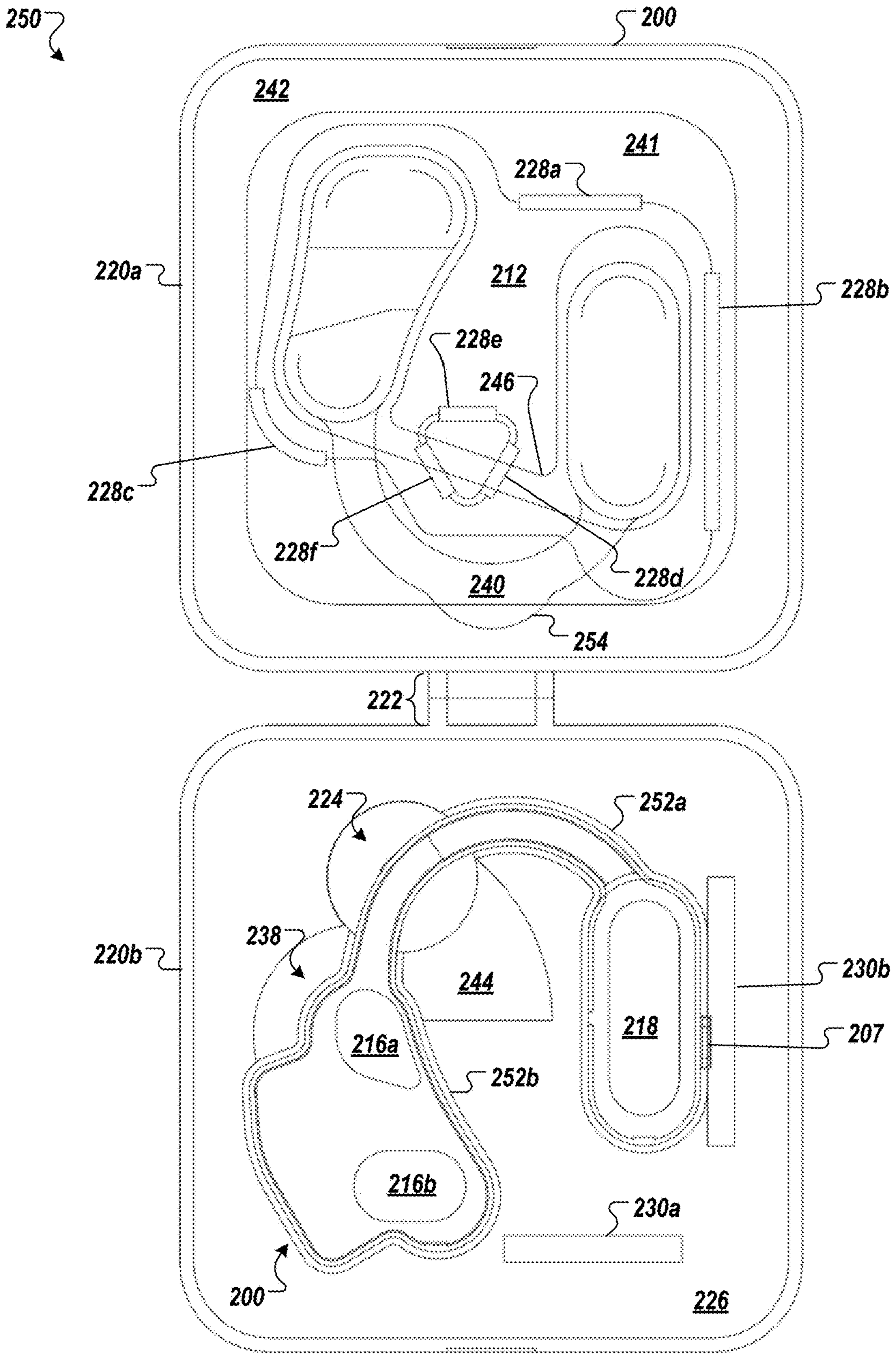
Figure 2D:
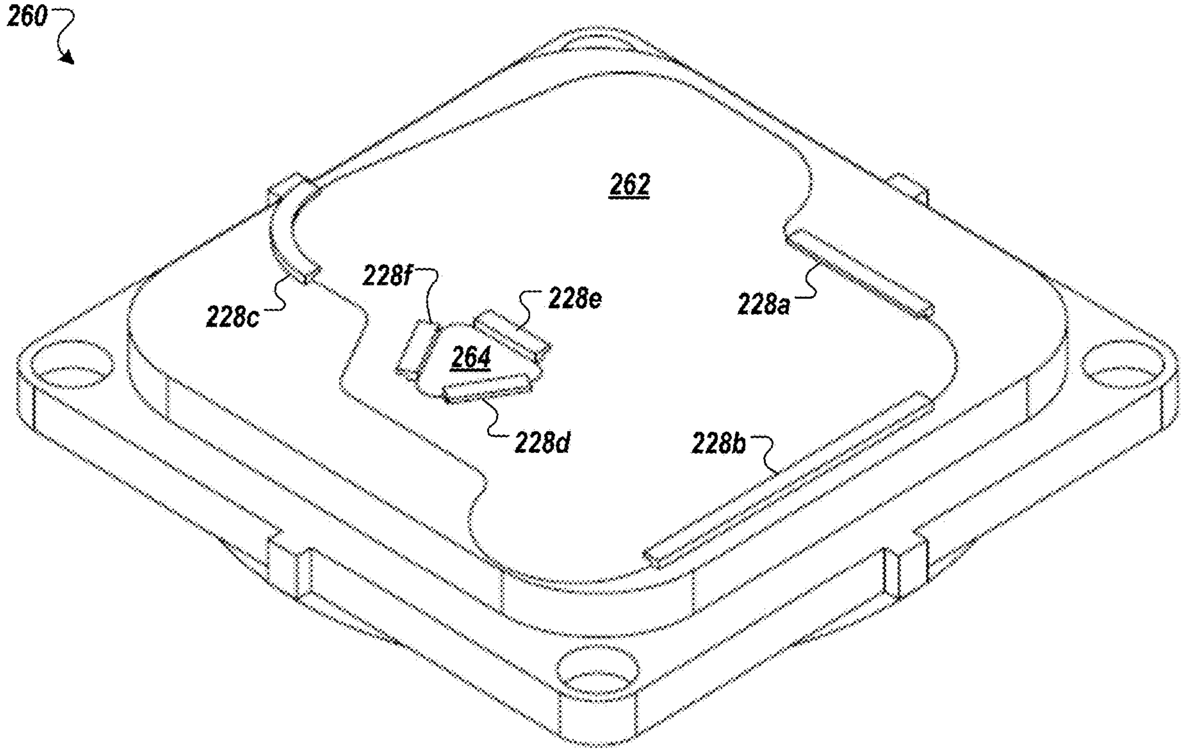

Turning to FIG. 2D, an offset view 260 of a portion of the first half 220*a* of the case 210 illustrates the raised geometry of the retention members 228. As shown in FIG. 2D, a first set of the retention members 228*a*, 228*b*, and 228*c* partially surround an electrode unit receiving depression 262 generally shaped to receive the disposable electrode assembly 212. A depression 264, shaped as a rounded triangle, may provide a finger hold to assist in adjusting the positioning of the disposable electrode assembly 212 and/or removing the disposable electrode assembly 212.

Returning to FIG. 2B, the alignment of the stimulation device 200 with the disposable electrode assembly 212 within the case 210, in some implementations, provides a precise loading mechanism for the disposable electrode assembly 212, ensuring proper alignment of the electrodes 232, 234, and 236*a,b* with the corresponding contacts 216*a*, 216*b*, and 218 of the stimulation device 200. In some embodiments, a cavity into which the stimulation device 200 is seated may include a perimeter lip having an internal shape corresponding to the geometry of the external edges of the disposable electrode assembly 212 such that the disposable electrode assembly 212 is configured to rest within the footprint of the perimeter lip of the depression in the second half 220*b* of the case 210 that receives the stimulation device 200. Turning to FIG. 2C, a top open view 250 of the case 210 provides an additional perspective of the elements described above in relation to FIG. 2B. As illustrated in FIG. 2C, for example, the stimulation device 200 is bordered, except when abutting the circular depression 224, with an extended outline 252 or "lip" that may be designed to receive at least a portion of the disposable electrode assembly 212. Returning to FIG. 2B, in some embodiments, the retention members 228*a*, 228*b*, when seated in the depressions 230*a*, 230*b*, may maintain relative positioning of the electrodes 232, 234, and 236*a,b* with the contacts 216*a*, 216*b*, and 218. Additionally, the curved retention member 228*c* near electrode 234 may align with an outer edge of a curved depression 238, and the triangularly arranged retention members 228*d-f* may align with a portion of a shallow depression 244 adjacent to the rounded opening 224.

Turning to FIG. 2C, when the case 210 is sufficiently open to access the first half 220*a* of the case 210 (e.g., for ease of use, in a fully opened (180 degrees) configuration as illustrated), the disposable electrode assembly 212 is loaded onto the first half 220*a* of the case 210 with its skin-side backing material 240 (e.g., liner) against the surface of the first half 220*a* of the case 210 and the device-side backing material 246 (e.g., liner) facing the user. The disposable electrode assembly 212 is retained, for example by inserting edge material of the disposable electrode assembly 212 beneath corresponding retention members 228*a-f* such that the retention members 228*a-f* extend over portions of the edge of at least the skin-side backing material 240. During loading, for example, the disposable electrode assembly 212 may be pressed into place, such that the skin-side backing material 240 bends where it meets the retention members 228*a-f*, then snaps back and extends again after being pushed past the overhang or "lip" of each of the retention members 228*a-f*. For easier installation, the skin-side backing material 240 may incorporate small cuts perpendicular to each of the retention members 228*a-f*, allowing it to bend more readily during insertion. The skin-side backing material 240, for example, may be formed of or include a rigid or semi-rigid plastic material, such as a three to five mil (e.g., 0.0765 to 0.0.127 millimeters) thick polyethylene terephthalate (PET), for sufficient strength to load the disposable electrode assembly 212. The small perpendicular cuts (e.g., 0.5 mm to 1.5 mm deep), for example, may provide selective adjustment to the rigidity of the plastic material. In another example, the skin-side backing material 240 may be formed of or include a fiber material such as a light cardboard.

In some implementations, to load the electrodes 232, 234, and 236 onto the contacts 216*a*, 216*b*, and 218 of the stimulation device 200, a user removes a device-side backing material 246 from the device-interfacing adhesive surfaces of the electrodes 232, 234, and 236 (e.g., the rear backing layer 108 of FIG. 1) and presses the first and second halves 220*a*, 220*b* of the case 210 together. When the user opens the case 210 after pressing the first and second halves 220*a*, 220*b* of the case 210 together, for example, the disposable electrode assembly 212 may be retained against the stimulation device 200 and released from the retention members 228*a-f*. The adhesion force between the contacts 216*a*, 216*b*, and 218 of the stimulation device 200 and the adhesive surfaces of the electrodes 232, 234, and 236, in an illustrative example, may exceed the force exerted by the retention members 228*a-f* on the disposable electrode assembly 212 by at least five percent. This force differential, for example, can be used to ensure that when the case is re-opened after contact, the disposable electrode assembly 212 remains attached to the stimulation device 200 rather than returning with the first half 220*a* of the case 210, thereby assuring transfer of the disposable electrode assembly 212 from the first half 220*a* of the case 210 to the stimulation device 200.

The case 210, in some implementations, incorporates one or more spring-loaded mechanisms to enhance the electrode transfer process. The spring-loaded mechanisms, for example, may assist in applying firm pressure to encourage adherence of the device-interfacing adhesive surfaces of the electrodes 232, 234, and 236 to the contacts 216*a*, 216*b*, and 218 of the stimulation device 200. In illustration, the spring-loaded mechanisms may maintain a space or gap between the adhesive surfaces of the electrodes 232, 234, and 236 and the contacts 216*a*, 216*b*, and 218 such that, by moving the first half 220*a* of the case 210 into alignment with the second half 220*b* of the case 210, the adhesive surfaces of the electrodes 232, 234, and 236 are maintained separated from the contacts 216*a*, 216*b*, and 218. In some examples, a user may press down on the halves of the case 210 and/or engage a locking mechanism of the case 210 to overcome a spring force of the spring-loaded mechanism(s).

In some embodiments, the case 210 incorporates a spring-loaded platform in the lid (e.g., the first half 220*a* of the case 210) that works in conjunction with the retention members 228*a-f* to enable precise electrode positioning and transfer. Turning to FIG. 2F, for example, a bottom view 280 of the case 210 illustrates a set of four springs 274*a-d* within the first half 220*a* of the case 210. The springs 274*a-d*, for example, may be configured to press an interior electrode unit-retaining platform 241 against a top frame 242 of the first half 220*a* of the case 210, ensuring a controlled distance between the disposable electrode assembly 212 and the stimulation device 200 when the case 210 is closed. In illustration, the distance between the disposable electrode assembly 212 and the stimulation device 200 may be between about 0.5 millimeters and 2.0 millimeters.

Figure 2E:
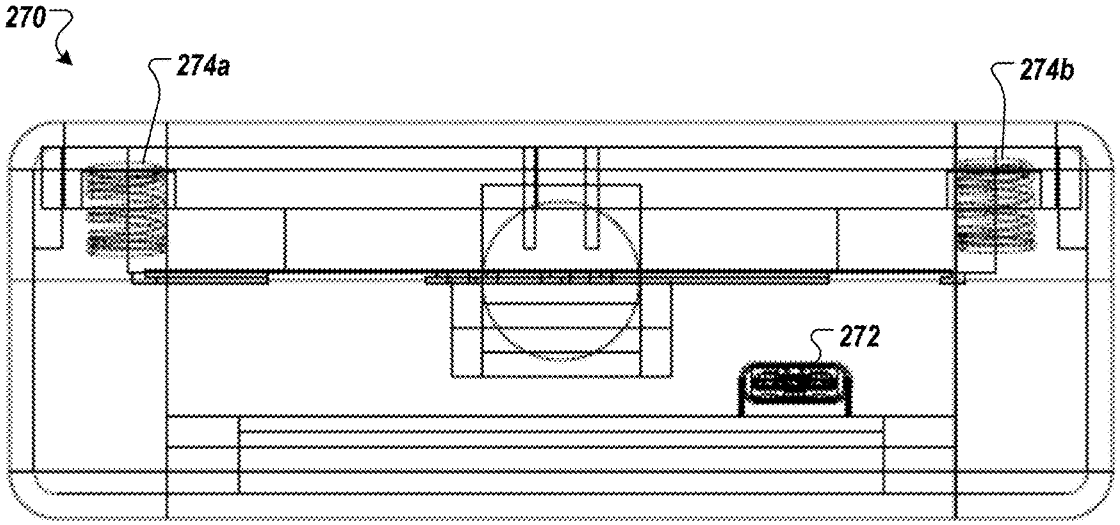
Figure 2F:
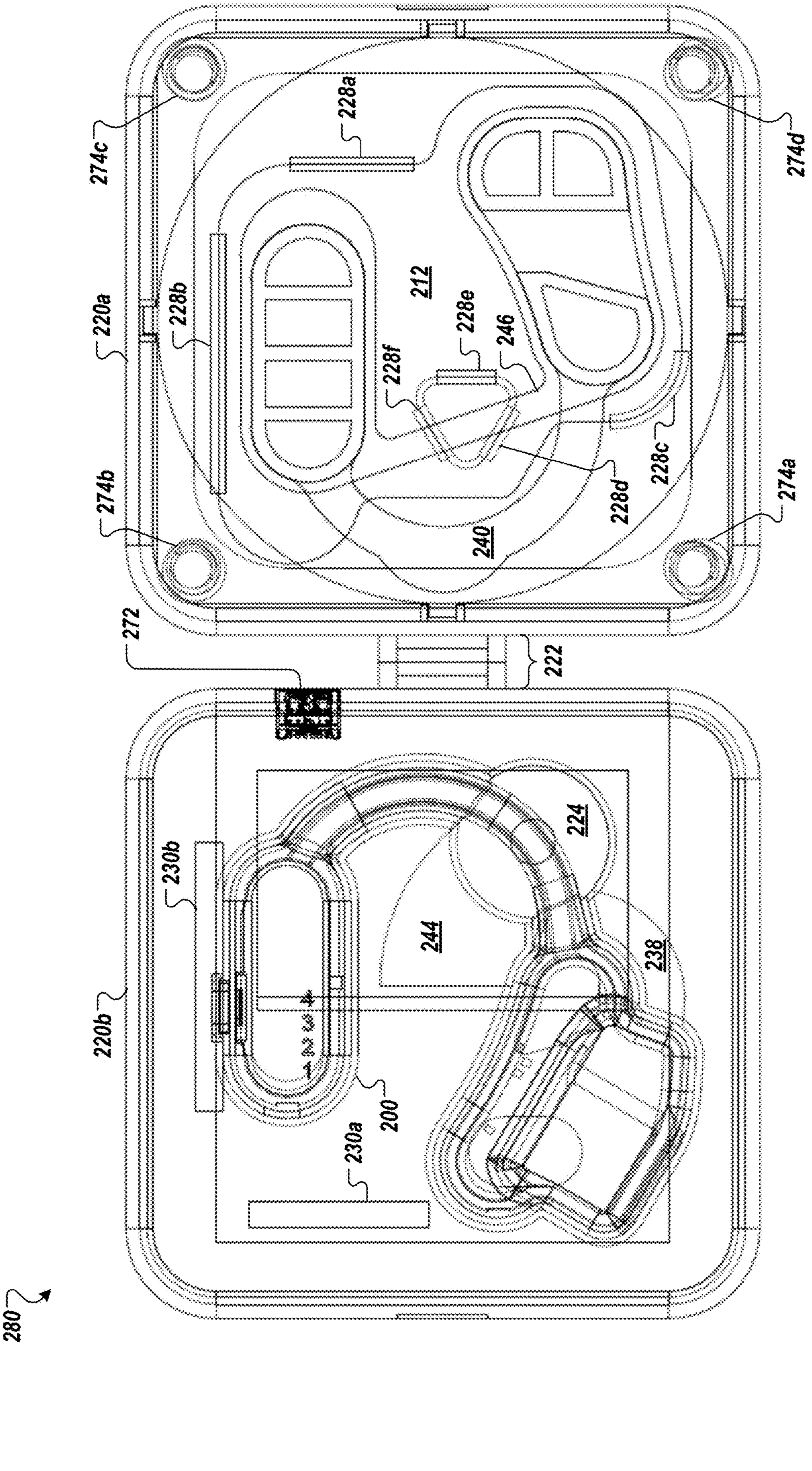

As illustrated in FIG. 2B through FIG. 2F, the case 210 is designed to serve dual functions: properly positioning the disposable electrode assembly 212 for transfer to the stimulation device 200 and providing a compact carrying case for the stimulation device 200 that is portable while providing robust protection for its contents. Further, in some implementations, the case 210 further acts as a convenient charging platform for the stimulation device 200. The case 210, for example, may incorporate safety features that eliminate the need for expensive isolation circuits in the stimulation device 200 itself. As FIG. 2E illustrates in a cutaway side view 270 of the case 210, for example, a charging port 272 may be provided to connect the case 210 to a power source, thereby allowing charging of the stimulation device 200 and/or recharging of a rechargeable battery of the case 210.

Figure 3:
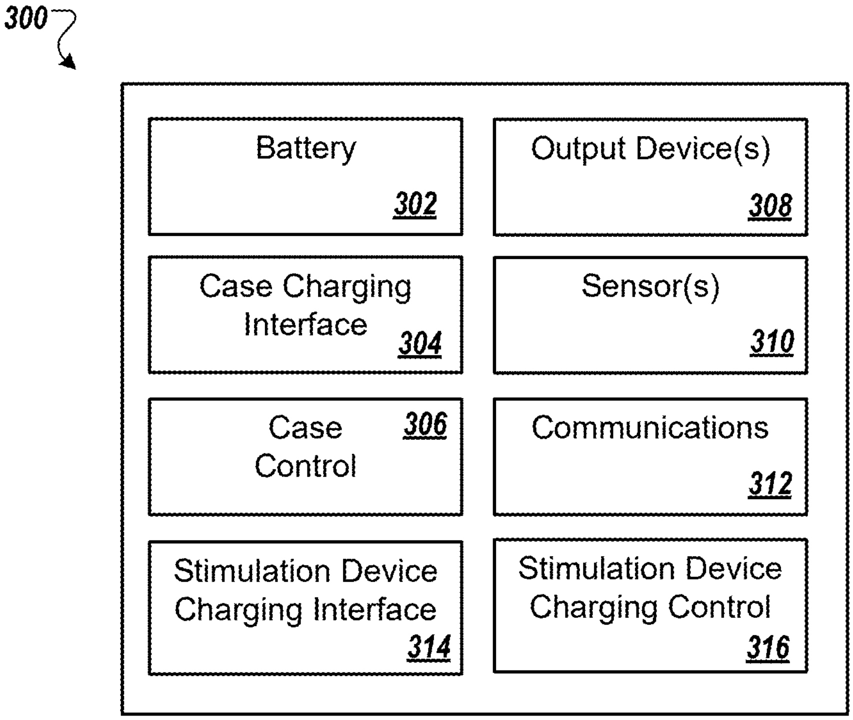
FIG. 3 is a block diagram of an electronic component system of a charging case for an electrical neurostimulation device.

Turning to FIG. 3, a block diagram illustrates an example electronic component system 300 of a charging case for an electrical neurostimulation device, such as the stimulation device 200 of FIG. 2A. The case 210 of FIG. 2B, FIG. 2C, and FIG. 2E, for example, may include the system 300 for supporting charging of the electrical neurostimulation device 200.

In some implementations, the system 300 includes a battery 302, such as one or more rechargeable batteries and/or non-rechargeable batteries. The battery 302, for example, may be a rechargeable battery in electrical communication with a case charging interface 304 and under recharging control of a case charging control unit 306. The case charging interface 304, for example, may include an electrical connector (e.g., USB, USB-C, microUSB, etc.) accessible via a wall of the case (e.g., the charging port 272 of FIG. 2E) and/or an inductive charging coil.

In some implementations, the case control unit 306 includes processing circuitry and at least one non-transitory computer-readable memory. The processing circuitry, in some examples, may include an application-specific integrated circuit (ASIC), a system on a chip (SoC), field programmable gate array (FPGA), and/or another customized or reprogrammable processing device (e.g., a microcontroller unit (MCU)) configured to execute operations for controlling the charging of the battery 302. In another example, the processing circuitry may include at least one processor configured to execute computer programming instructions, such as instructions stored to the memory. The memory, in some examples, may include one or more flash memory devices, dynamic random-access memory (DRAM) devices, non-volatile random-access memory (NVRAM) devices, and/or static random-access memory (SRAM) devices. In another example, the memory may be incorporated into the processing circuitry as an on-chip memory unit.

The battery 302, in some implementations, is configured to power one or more elements of the charging case, such as output device(s) 308. For example, the battery 302 may provide power to illuminate one or more external and/or internal lights for communicating information to the user, such as one or more light emitting diodes (LEDs) for indicating a state of charge of the stimulation device held by the charging case and/or the state of charge of the battery 302. In another example, the battery 302 may provide power to one or more speakers or sound elements of the output device(s) 308 to provide a sound indication, such as one or more warning tones regarding battery charge, device charge, and/or device orientation within the storage case.

In some implementations, the battery 302 powers one or more sensors 310. The sensor(s) 310, in a first example, may include at least one sensor for identifying proper insertion of the stimulation device and/or a disposable electrode assembly into the charging case. In another example, the sensor(s) 310 may include at least one sensor for identifying proper attachment of the disposable electrodes of the disposable electrode assembly to the stimulation device. In a further example, one or more sensors 310 may be positioned to detect insertion of a stimulation device with a used disposable electrode unit still attached, for example to avoid the circumstance of a new disposable electrode unit being adhered to a previously used disposable electrode unit.

The battery 302, in some implementations, powers at least one communications element 312. The communications element(s) 312 may include at least one short-range wireless communications device configured to communicate in one or more short-range wireless communications technologies such as, in some examples, Bluetooth®, low power Bluetooth®, or Zigbee. The communications element(s) 312 may be configured to communicate with the controller (e.g., controller 208 of FIG. 2A) of the stimulation device and/or another portable computing device, such as a smart phone. In illustration, a charge level of the stimulation device may be monitored by a user via a smart phone app receiving charge level data from the system 300 via the communication element(s) 312.

The communications element(s) 312, in some implementations, include communications control processing circuitry for establishing communications with the stimulation device and/or another portable computing device. The communications control operations may be performed by the processing circuitry of the case charging interface 304 or the system 300 may incorporate additional hardware to support the communications control operations.

In some implementations, the system 300 includes a stimulation device charging interface 314 for transferring charge from the battery 302 (and/or a power source connected via the case charging interface 304) to the stimulation device. The stimulation device charging interface 314, for example, may include one or more electrical connectors, such as conductive contacts that align with conductive contacts of the stimulation device when the stimulation device is seated in the charging case. In another example, the stimulation device charging interface 314 may include an inductive charging coil formed within the charging case.

In some implementations, the system 300 includes a stimulation device charging control unit 316 for controlling the charging of the stimulation device. The stimulation device charging control may be performed by the processing circuitry of the case charging interface 304, or the system 300 may incorporate additional hardware to support the stimulation device charging control operations (e.g., a portion of the case control 306). The stimulation device charging control unit 316, for example, may include a DC/DC converter such that the output voltage at the stimulation device charging interface 314 remains constant regardless of the present voltage of the battery 302. The current, further to the example, can vary depending on the battery of the stimulation device. In another example, the stimulation device charging control unit 316 may include overvoltage protection circuitry to safely charge the battery 302 and/or the battery of the stimulation device. The overvoltage protection circuitry may be provided by one or more commercially available overvoltage protection circuits, such as an overvoltage protection circuitry manufactured by Analog Devices, Inc. of Wilmington, MA or Texas Instruments of Dallas, Texas.

In some implementations, the case control unit 306 oversees the functionality of other elements of the system 300, such as, in some examples, monitoring a charge level of the battery 302, managing messaging via the output device(s) 308 (e.g., indicator lights regarding battery charge level), managing communications flow via the communications element(s) 312, and/or analyzing and responding to sensor input captured by the sensor(s) 310. In some embodiments in which LEDs are used to communicate the charge level/status of the batteries, the LEDs can reflect the battery status of the case when the stimulation device is not inside the case. In this example, inserting the stimulation device 200 into the case 210 of FIG. 2B would cause the LEDs to switch into displaying the battery status of the stimulation device 200 instead of that of the battery of the case 210. In further embodiments, separate sets of LEDs are used to communicate the status of the stimulation device battery and the case battery (e.g., battery 302).

Figure 4:
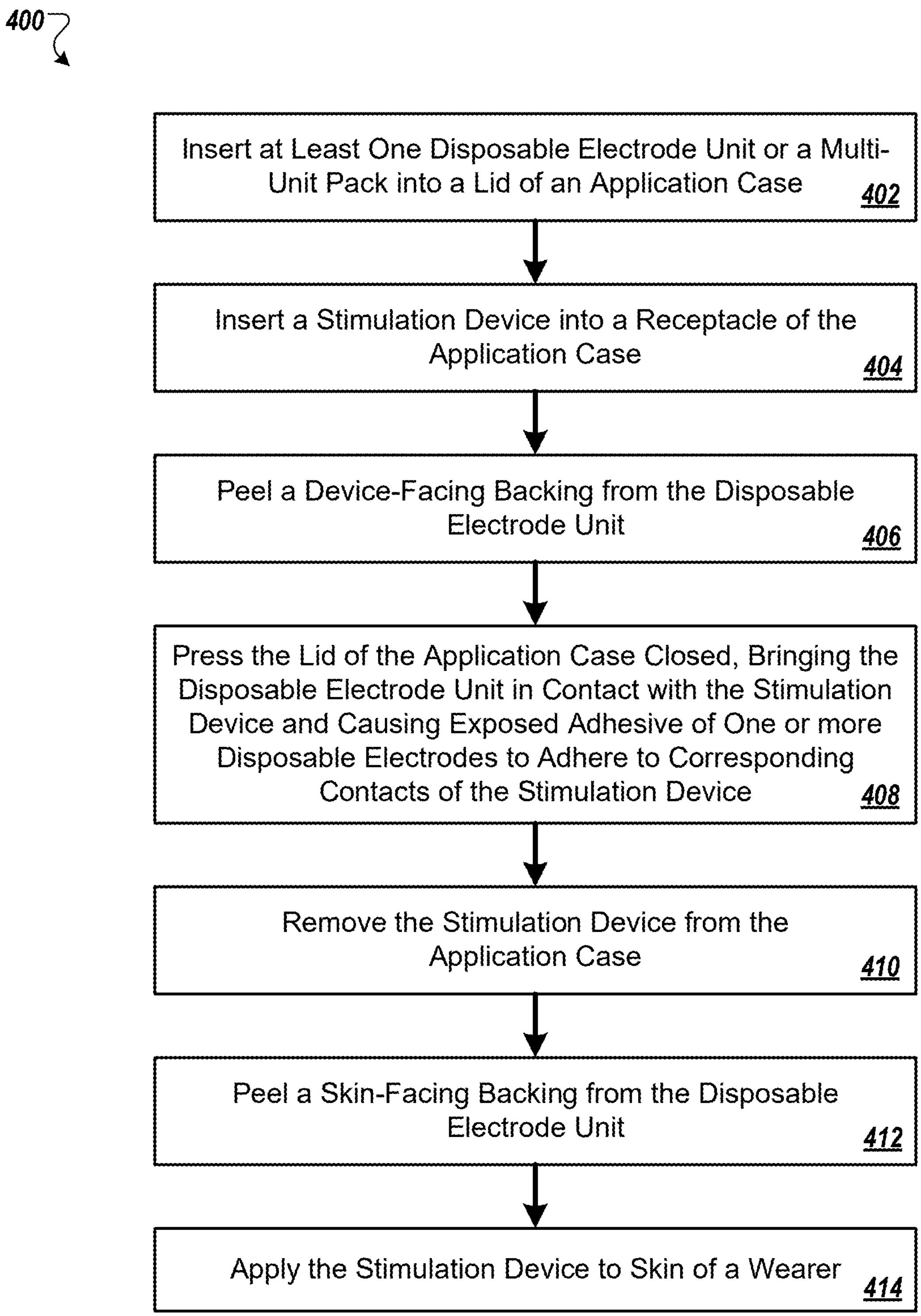
FIG. 4 is a flow chart of an example method for using a disposable electrode application case in installing electrodes to a wearable neurostimulation device.

Turning to FIG. 4, a flow chart illustrates an example method 400 for using a disposable electrode application case in installing electrodes to a wearable neurostimulation device. The method 400, for example, may be used for installing the disposable three-electrode unit 100 of FIG. 1 onto the stimulation device 200 of FIG. 2A using the case 210 of FIG. 2B and FIG. 2C.

In some implementations, the method 400 begins with inserting at least one disposable electrode unit or a multi-unit pack containing multiple disposable electrode units into a lid of an application case (402). The lid, for example, may be designed to releasably secure at least one disposable electrode unit. With multiple disposable electrode units, the units may be stacked to store two or more units in a releasable manner. A pack, for example, may be used to conveniently install multiple disposable electrode units at once. The pack, for example, may be formed as a dispensing cartridge. In an illustrative example, the disposable electrode unit 212 may be installed in the first half 220*a* of the case 210 of FIG. 2B and FIG. 2C using the set of retention members 228*a-f*.

In some implementations, a stimulation device is inserted into a receptacle of the application case (404). The stimulation device, for example, may be set within one or more depressions in an opposite side of the application case to the lid, such that the stimulation device is aligned with the disposable electrode unit. In illustration, the stimulation device 200 of FIG. 1 may be set in the second half 220*b* of the case 210 within a depression such that a majority of the stimulation device 200 is disposed beneath or aligned with the interior surface 226 of the second half 220*b* of the case 210.

In some implementations, a device-facing backing is peeled from the disposable electrode unit (406). The device-facing backing, for example, may be a plastic, wax-lined or siliconized paper, or other protective surface designed to avoid exposure of adhesive surfaces of the device-facing side of the disposable electrode unit from contamination (e.g., dust, oils, liquids, oxidation, etc.). A user, for example, may grasp an extension (e.g., the connecting portion 114 as illustrated in FIG. 1) of the device-side backing material 246 (illustrated in FIG. 2C) that extends beyond a perimeter of the underlying electrode unit to peel the device-side backing material 246 from the disposable electrode unit 212.

In some implementations, after the device-facing backing material is removed from the disposable electrode unit, the lid of the application case is closed, bringing the disposable electrode unit in contact with the stimulation device and causing exposed adhesive of one or more disposable electrodes of the disposable unit to adhere to corresponding contacts of the stimulation device (408). Turning to FIG. 2B, a user, for example, may close the first half 220*a* of the case 210 against the second half 220*b* of the case 210 to bring the exposed adhesive portions of the electrodes 232, 234, and 236*a,b* of the disposable electrode unit 212 into contact with the contacts 216*a*, 216*b*, and 218 of the stimulation device 200. Upon closing the case 210 and/or pressing the halves 220*a*, 220*b* of the case 210 together (e.g., in the circumstance of a spring-loaded lid), for example, the retention members 228*a*, 228*b* are received by the corresponding depressions 230*a*, 230*b*, the retention member 228*c* is received by the curved depression 238, and the retention members 228*d*, 228*e*, and 228*f* are received by the shallow depression 244, thereby allowing for precise alignment of the disposable electrode unit 212 against the stimulation device 200. A spring-loaded lid, in this example, may ensure firm contact between the adhesive of the disposable electrode unit 212 and the contacts of the stimulation device 200. In some embodiments, the spring-loaded lid needs to be pressed in order to bring the disposable electrode into contact with the stimulation device; that is, upon closing the case, the stimulation device 200, in particular the contacts

216*a*, 216*b*, and 218, are not touching the disposable electrode 212 until the spring-loaded lid is pressed, in some cases by the user's hand.

In some implementations, the stimulation device is removed from the application case (410). The stimulation device may be removed immediately or at some other time (e.g., when a next session of the stimulation therapy is desired). When the user opens the case (e.g., pulls the first half 220*a* of the case 210 away from the second half 220*b* of the case 210, the strength of adherence of the disposable electrode unit 212 to the contacts of the stimulation device 200 may overcome the retention force asserted by the retention members 228 to retain the disposable electrode unit 212 firmly against the stimulation device 200. To remove the stimulation device 200 from the case 210, for example, a user may reach within the depression 238 and/or 224 to overcome any retention provided by the depression in the second half 220*b* of the case 210 and grasp the over-the-ear connector 206 to lift the stimulation device 200 from the case 210.

In some implementations, a skin-facing backing is peeled from the disposable electrode unit (412). The skin-facing backing, for example, may be a siliconized plastic, wax-lined paper, or other protective surface designed to avoid exposure of adhesive surfaces of the skin-facing side of the disposable electrode unit from contamination (e.g., dust, oils, liquids, oxidation, etc.). A user, for example, may grasp a section of the skin-side backing material 240 (illustrated in FIG. 2C, also illustrated as the front backing layer 110 of FIG. 1) that extends from or is not aligned with a perimeter of the stimulation device, such as the opening 116 or a rounded feature 118 of the front backing layer 100 of FIG. 1, to peel the skin-side backing material 240 from the disposable electrode unit 212.

In some implementations, the stimulation device is applied to the skin of a wearer (414). The electrodes of the stimulation device, for example, may be applied to the skin of the wearer to align the electrodes with target nerve structures. In illustration, the stimulation device 200, for example, may be applied over the ear of a wearer.

Although described in relation to a particular set of operations, in other embodiments, the method 400 may include more or fewer operations. For example, the method 400 may include removing a previously applied disposable electrode unit prior to inserting the stimulation device into the receptacle of the application case (404). Removal, for example, may include manually peeling the prior disposable electrode unit from the stimulation device. The manual peeling, in illustration, may be enabled in part using a grip section 254 (illustrated in FIG. 2C) extending beyond a perimeter of the stimulation device 200. In a further example, rather than peeling the skin-facing backing from the disposable electrode unit (412), in embodiments, the skin-facing backing releases upon opening the case. For example, a feature of the lid of the application case or a feature of a multi-unit pack including the disposable electrode unit may retain the skin-side backing material upon opening of the application case.

Although described in relation to a particular order of operations, in other embodiments, certain operations of the method 400 may be performed in a different order or concurrently. For example, the device-facing backing may be peeled from the disposable electrode unit (406) prior to inserting the stimulation device into the receptacle (404). In another example, the stimulation device may be inserted into the receptacle (404) prior to inserting the disposable electrode unit(s) into the lid of the application case (402). Other modifications of the method 400 are possible.

In the circumstance where a user failed to remove a prior disposable electrode unit before closing the stimulation device within the application case, in some implementations, the application case includes one or more features for preventing application of an additional disposable electrode unit upon a previously applied disposable electrode unit. The disposable electrode unit, for example, may extend beyond at least a portion of a perimeter of the stimulation device such that the application case will not close properly if the prior disposable electrode unit is not first removed. In illustration, the extension 254 shown in FIG. 2C extends beyond the top frame 242 of the first half 220*a* of the case 210 such that, upon closing, the extension 254 would prevent contact between the top frame 242 of the case 210 and the bottom frame 226 of the case 210. In preventing the case from fully closing, for example, closing the case may prevent secure adhesion of a new disposable electrode unit to a previously applied disposable electrode unit.

In some implementations, the case may be designed to detect a previously applied disposable electrode unit. For example, one or more sensors may be disposed within the case to recognize presence of a disposable electrode unit attached to the stimulation device. The sensors, for example, may be the sensors 310 of FIG. 3. The case control unit 306 of the system 300 may analyze output of the sensor(s) to prevent application of a new disposable electrode unit upon a used disposable electrode unit still attached to the stimulation device. Preventing a doubled-up attachment, in some examples, may include issuing one or more alerts from the output device(s) 308 (e.g., an audible alarm and/or flashing illumination), preventing the case from fully closing, and/or locking a disposable electrode unit pack so that a next disposable electrode unit will not be released.

Figure 5B:
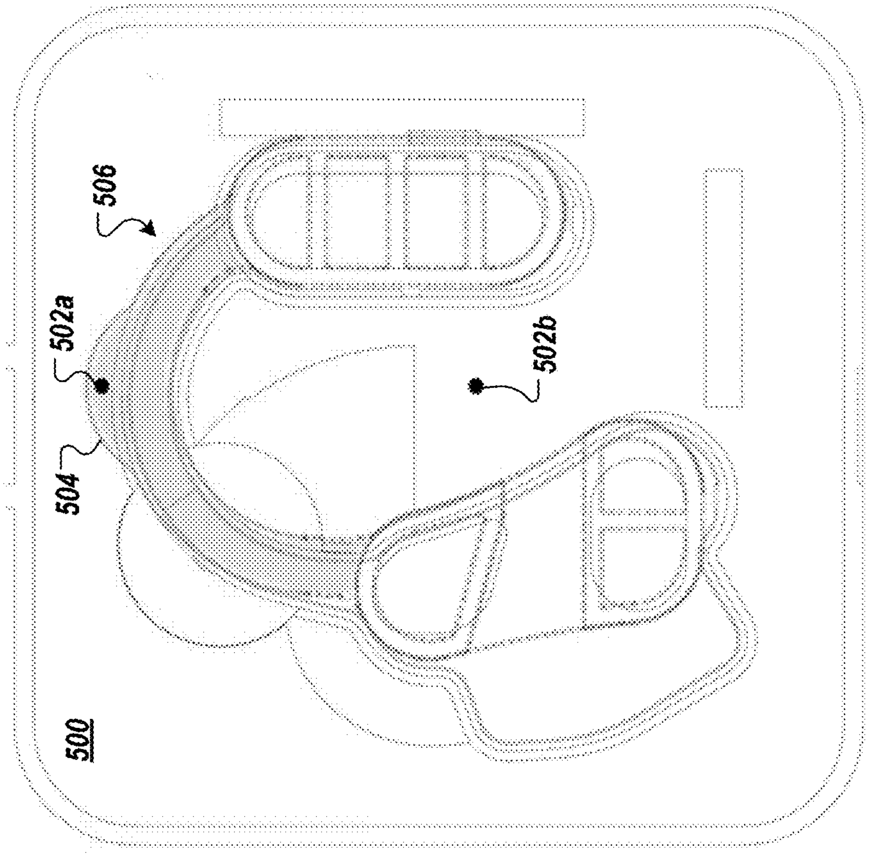
FIG. 5A and FIG. 5B are diagrams of an example sensor system arranged in a case for installing disposable electrodes onto a stimulation device.
Figure 5A:
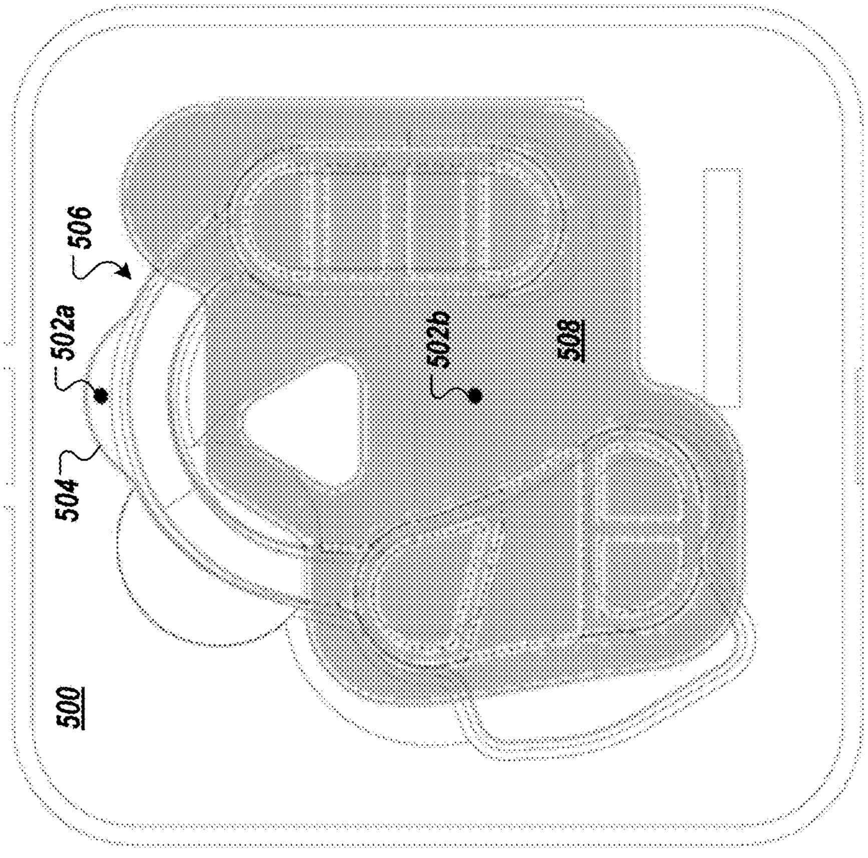

Turning to FIG. 5A and FIG. 5B, in some implementations, a case 500 includes a set of sensors 502*a*, 502*b* configured to detect presence of a disposable electrode attached to a stimulation device 506. The sensors 502*a*, 502*b*, for example, may be proximity sensors. The sensors 502*a*, 502*b*, for example, may be aligned to detect both a feature of a new disposable electrode unit (e.g., retaining at least one backing material layer) and a feature of a previously applied (e.g., used) disposable electrode unit (e.g., lacking either backing material layer). The sensors 502*a*, 502*b*, in some embodiments, may be disposed in or beneath an upper surface of a stimulation device retaining side (e.g., base) of the application case 500.

Turning to FIG. 5A and FIG. 5B, in some implementations, a first sensor 502*a* is disposed in a region of the case 500 where no portion of the stimulation device 506 would cover the first sensor 502*a* but where a feature 504 of a disposable electrode unit, if present, would cover the first sensor 502*a*. The feature 504, for example, may be the grasping feature used to remove the disposable electrode unit from the stimulation device 506 after use.

As illustrated in FIG. 5A and FIG. 5B, in some implementations, a second sensor 502*b* is disposed in a region of the case 500 where no portion of the stimulation device 506 would cover the second sensor 502*b* but where a backing material layer 508, if present, would cover the second sensor 502*b*. As illustrated in FIG. 5A the skin-facing backing layer 508 (e.g., the backing layer 110 of FIG. 1) is positioned on the stimulation device 506. In this example, a disposable electrode unit may have been installed on the stimulation device 506, but the stimulation device 506 has never been applied to a wearer.

In some implementations, when the case 500 is open, a controller (e.g., processing circuitry, such as the case control unit 306 of the system 300 of FIG. 3) may analyze outputs of each of the sensors 502*a,b* to determine whether one or both of the sensors 502*a,b* detect presence of a disposable electrode unit.

When the first sensor 502*a* and the second sensor 502*b* both detect the presence of an overlying feature, in some embodiments, the controller may recognize the disposable electrode unit as a new, never applied disposable electrode unit. Upon closing the case, in some embodiments, the controller may prevent release of a next disposable electrode unit upon identifying presence of a new disposable electrode unit. For example, the controller may lock a disposable electrode pack to prevent release of a next disposable electrode unit.

When the first sensor detects the presence of an overlying feature, but the second sensor 502*b* fails to detect an overlying feature, in some embodiments, the controller may recognize the disposable electrode unit as a used disposable electrode unit. To prevent application of another disposable electrode unit, the controller may issue a warning to a user to prompt the user to remove the disposable electrode unit. The warning, in some examples, may include an audible, visual, and/or tactile alert provided via one or more output devices of the case. Further, if the user proceeds with closing the case, the controller may prevent release of a next disposable electrode unit. For example, the controller may lock a disposable electrode pack to prevent release of a next disposable electrode unit.

While certain embodiments have been described, these embodiments have been presented by way of example only and are not intended to limit the scope of the present disclosure. Indeed, the novel methods, apparatuses and systems described herein can be embodied in a variety of other forms; further, various omissions, substitutions and/or changes in the form of the methods, apparatuses and systems described herein can be made without departing from the spirit of the present disclosure. The accompanying claims and their equivalents are intended to cover such forms or modifications as would fall within the scope and spirit of the present disclosure.

What is claimed is:

1. A disposable electrode unit for releasably adhering to a wearable auricular stimulation device, the disposable electrode unit comprising:
- a structural support layer having an asymmetric shape configured to wrap partially around an ear of a wearer, the structural support layer comprising a plurality of openings configured to align with a plurality of electrode contacts of the wearable auricular stimulation device; and
- one or more adhesive layers, each respective adhesive layer of the one or more adhesive layers being composed of one or more materials, wherein
  - the one or more materials comprises a conductive material configured to provide at least one of electrical conductivity or adhesion, and
  - the one or more adhesive layers are disposed to fill the plurality of openings, thereby enabling electrical conduction from the plurality of electrode contacts to tissue regions on and/or surrounding the ear of the wearer while the disposable electrode unit is attached to the wearable auricular stimulation device and the wearable auricular stimulation device is donned by the wearer;
  - wherein a device-facing surface of the one or more adhesive layers is configured to releasably adhere to one or more surfaces of the wearable auricular stimulation device including the plurality of electrode contacts; and
  - wherein a skin-facing surface of the one or more adhesive layers is configured to releasably adhere to the tissue regions on and/or surrounding the ear of the wearer.

2. The disposable electrode unit of claim 1, further comprising:
- a skin-facing backing layer covering the skin-facing surface of the one or more adhesive layers; and
- a device-facing backing layer covering the device-facing surface of the one or more adhesive layers.

3. The disposable electrode unit of claim 1, wherein the structural support layer is formed of one or more biocompatible plastics.

4. The disposable electrode unit of claim 1, wherein the structural support layer is formed of flexible material to conform to anatomical surfaces on and/or surrounding the ear of the wearer.

5. The disposable electrode unit of claim 1, wherein:
- the one or more adhesive layers consists of a single adhesive layer; and
- the plurality of openings comprise a perforated design to increase a surface area of the structural support layer, thereby enhancing adhesion between the single adhesive layer at the structural support layer.

6. The disposable electrode unit of claim 1, wherein the skin-facing surface of the one or more adhesive layers is composed of a same adhesive material as the device-facing surface of the one or more adhesive layers.

7. The disposable electrode unit of claim 1, wherein the one or more adhesive layers comprises:
- a device-side adhesive layer adhered to a device-facing side of the structural support layer; and
- a skin-side adhesive layer adhered to a skin-facing side of the structural support layer.

8. The disposable electrode unit of claim 7, wherein the device-side adhesive layer is composed of a dry conductive adhesive.

9. The disposable electrode unit of claim 7, wherein the skin-side adhesive layer is composed of a repositionable material allowing for repositioning of the wearable auricular stimulation device on the wearer prior to activation of full adhesive properties of the repositionable material.

10. The disposable electrode unit of claim 1, wherein the one or more adhesive layers comprises one or more adhesive materials for maintaining secure adhesion of the wearable auricular stimulation device to the wearer for at least four hours.

11. The disposable electrode unit of claim 1, wherein:
- the disposable electrode unit is configured to releasably stack against one or more additional disposable electrode units in a dispensing cartridge; and
- the disposable electrode unit comprises one or more retention features configured to be releasably received by one or more surfaces of the dispensing cartridge.

12. The disposable electrode unit of claim 9, wherein the repositionable material achieves full adhesive properties after warming to body temperature.

13. The disposable electrode unit of claim 5, wherein the perforated design causes at least part of the structural support layer to form at least one of a mesh, a grid, or a honeycomb pattern.

14. The disposable electrode unit of claim 1, wherein the structural support layer comprises a grip section configured to extend beyond a shape of the wearable auricular stimulation device when adhered to the one or more surfaces of the wearable auricular stimulation device.

* * * * *